| (12) United States Patent | (10) Patent No.: US 8,625,864 B2 |
|---|---|
| Goodman | (45) Date of Patent: Jan. 7, 2014 |

(54) SYSTEM AND METHOD OF COSMETIC ANALYSIS AND TREATMENT DIAGNOSIS

(76) Inventor: Gregory Goodman, South Yarra (AU)

( * ) Notice: Subject to any disclaimer, the term of this patent is extended or adjusted under 35 U.S.C. 154(b) by 270 days.

(21) Appl. No.: 12/866,636

(22) PCT Filed: Feb. 12, 2009

(86) PCT No.: PCT/AU2009/000166

§ 371 (c)(1),
(2), (4) Date: Aug. 6, 2010

(87) PCT Pub. No.: WO2009/100494

PCT Pub. Date: Aug. 20, 2009

(65) Prior Publication Data

US 2010/0329525 A1  Dec. 30, 2010

(30) Foreign Application Priority Data

Feb. 14, 2008  (AU) ................. 2008900695

(51) Int. Cl.
*G06K 9/00*  (2006.01)
(52) U.S. Cl.
USPC .......................... 382/128; 600/306
(58) Field of Classification Search
USPC .......................... 382/128; 600/300
See application file for complete search history.

(56) References Cited

U.S. PATENT DOCUMENTS

| 2004/0215066 A1 | 10/2004 | Huang et al. |
| 2005/0197542 A1* | 9/2005 | Bazin et al. ................... 600/300 |
| 2007/0086651 A1 | 4/2007 | Stephan et al. |
| 2008/0194928 A1* | 8/2008 | Bandic et al. ................. 600/306 |

FOREIGN PATENT DOCUMENTS

WO  00/76398 A1  12/2000

* cited by examiner

*Primary Examiner* — Brian Q Le
*Assistant Examiner* — Michael Vanchy, Jr.
(74) *Attorney, Agent, or Firm* — David A. Guerra

(57) ABSTRACT

A method and system is provided for performing cosmetic analysis of a subject. Assessment data of observable characteristics of each of a plurality of defined body areas of a subject is converted to weighted data for each of the plurality of defined body areas. This weighted data is analyzed to generate cosmetic analysis data. This cosmetic analysis data can include an apparent age of the subject. The cosmetic analysis data is then provided to a user such as a cosmetic surgeon, beauty therapist or the subject themself. The system and method can be further adapted to perform treatment diagnosis for the subject based on the cosmetic analysis data.

20 Claims, 4 Drawing Sheets

SYSTEM AND METHOD OF COSMETIC ANALYSIS AND TREATMENT DIAGNOSIS

CROSS-REFERENCE TO RELATED APPLICATIONS

This application is an U.S. national phase application under 35 U.S.C. §371 based upon co-pending International Application No. PCT/AU2009/000166 filed on Feb. 12, 2009. Additionally, this U.S. national phase application claims the benefit of priority of co-pending International Application No. PCT/AU2009/000166 filed on Feb. 12, 2009, and Australia Application No. 2008900695 filed on Feb. 14, 2008. The entire disclosures of the prior applications are incorporated herein by reference. The international application was published on Aug. 20, 2009 under Publication No. WO 2009/100494.

TECHNICAL FIELD

The present invention relates to cosmetic analysis of skin characteristics. An example of an application of an embodiment of the present invention is for analysing the apparent age of a person's skin.

BACKGROUND OF THE INVENTION

It is known for cosmetic surgeons and beauticians to treat characteristics of a person's skin which alter with age or health, such a wrinkling and discoloration, in order to minimise apparent aging of the person.

It is known to use "before" and "after" pictures in order to demonstrate the apparent effect a treatment may have on a person. However, it is difficult to quantify the actual difference between "before and after" pictures. There is also a negative perception about the use of "before and after" pictures within the cosmetic treatment industry and governing bodies as such "before and after" demonstrations can be used in a misleading manner.

There is a need for a quantifiable analysis of characteristics of a person's appearance for use in the cosmetic treatment industry.

SUMMARY OF INVENTION

According to one aspect of the present invention there is provided a cosmetic analysis system comprising:
  an input interface adapted to receive assessment data of observable characteristics of each of a plurality of defined body areas of a subject;
  a cosmetic analysis module adapted to convert the assessment data for each of the plurality of defined body areas to weighted data associated with each body area and generate cosmetic analysis data from the weighted data; and
  an output interface adapted to output the cosmetic analysis data.

According to another aspect of the present invention there is provided a cosmetic analysis method comprising the steps of:
  receiving assessment data of observable characteristics of each of a plurality of defined body areas of a subject;
  converting the assessment data for each of the plurality of defined body areas to weighted data associated with each body area;
  generating cosmetic analysis data from the weighted data; and
  outputting the cosmetic analysis data.

The cosmetic analysis data can include an overall subject apparent age value for the subject.

In an embodiment assessment data for each area of the body is based on apparent age of the area of the body.

In an embodiment converting the assessment data comprises:
  determining from the assessment data an aging rating value for each area; and
  applying to each aging rating value a weighting for the area relating the contribution of the aging rating of the area to an overall subject apparent age to provide weighted data for the area.

The applied weighting for each area of the body can be further based on subject gender. The applied weighting for each area of the body can be further based on subject ethnicity.

Generated cosmetic analysis data can identify one or more body areas significantly influencing the overall subject apparent age value. Identifying the body areas significantly influencing the overall subject apparent age value can be based on comparing the actual age of the subject with the overall subject apparent age value.

Generated cosmetic analysis data can include data ranking body areas based on relative contribution to the overall subject apparent age value.

An embodiment of the system further comprises a treatment diagnosis module adapted to determine one or more suggested treatments for each of one or more body areas and output suggested treatment data. Suggested treatments can be ranked based on given criteria. The given criteria may be specified by a user.

Ranking suggested treatments may also be based on influence of the body area for which the treatment is suggested on overall subject apparent age.

The treatment diagnosis module can be further adapted to develop a treatment plan for the subject. The treatment plan can be based on selected criteria. For example the criteria may include one or more of subject permitted surgical and non surgical criteria, complementary treatment grouping, body area treatment grouping and specified treatment or recovery times.

In an embodiment subject assessment data is obtained from a subject survey. For example, the survey may be conducted as a self assessment by a subject or completed by a subject during a consultation with a therapist or cosmetic surgeon. In an embodiment of the system the input interface receives assessment data from the results of a survey taken by the subject.

BRIEF DESCRIPTION OF THE DRAWINGS

An embodiment, incorporating all aspects of the invention, will now be described by way of example only with reference to the accompanying drawings in which
  FIG. 1 A block diagram of an embodiment of a cosmetic analysis system.

DETAILED DESCRIPTION

Figure 1:
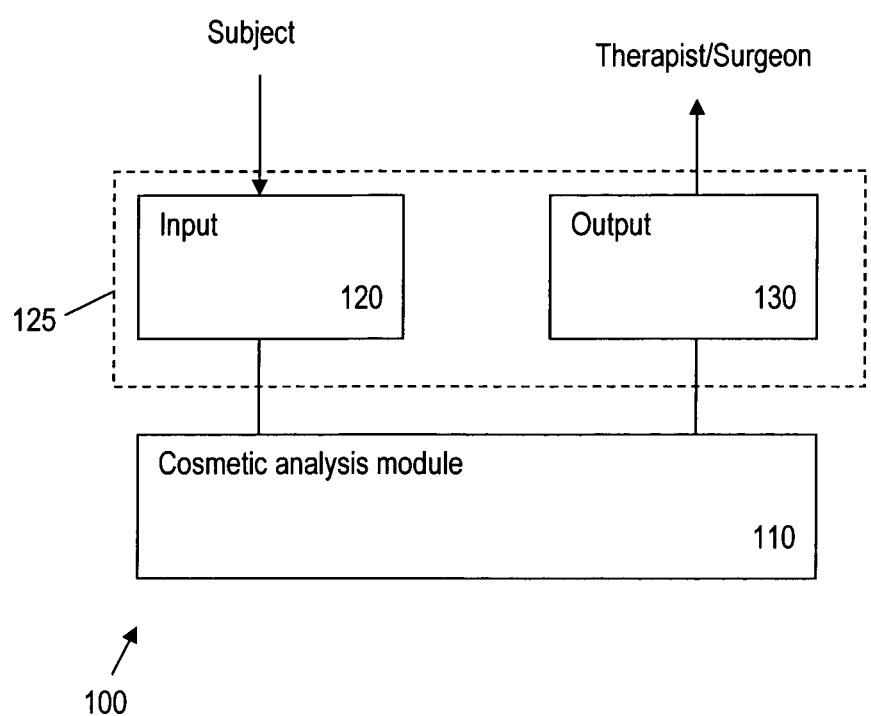

Embodiments of the present invention provide a method and system for performing cosmetic analysis of a subject.

Assessment data of observable characteristics of each of a plurality of defined body areas of a subject is received. The assessment data is converted to weighted data for each of the plurality of defined body areas. This weighted data is analysed to generate cosmetic analysis data. This cosmetic analysis data can include an apparent age of the subject. The cosmetic analysis data is then provided to a user such as a cosmetic surgeon, beauty therapist or the subject themself.

The cosmetic analysis system comprises a cosmetic analysis module 110, and input interface 120 and an output interface 130. The input interface 120 is adapted to receive assessment data of observable characteristics of each of a plurality of defined body areas of a subject. The cosmetic analysis module 110 is adapted to convert the assessment data for each of the plurality of defined body areas to weighted data associated with each body area. The weighting for each body area relates the assessed aging of the body area, based on the observed characteristics, in combination with the contribution of this assessed aging to an overall apparent age for the subject.

The cosmetic analysis module 110 then analyses the weighted data to generate cosmetic analysis data. The cosmetic analysis data is then output via the output interface 130. In some embodiments the input interface 120 and output interface 130 may be provided as a combined input/output interface 125.

The human body can be divided into a plurality of areas such that each body area is associated with an observable characteristic, the size of the body areas may vary. The body areas can be defined by the features associated with the observable characteristics. For example, a body area may be defined as the facial under eye area associated with bags and discoloration, also known as dark circles. This area is known to cosmetic surgeons and therapists as the infraorbital area. Typical aging problems with this area are lines under the eyes and fat pads in the lower eye lid. This infraorbital area is separately defined and assessed from the area around the outer corner of the eye associated with wrinkles known as "crows feet", the upper eye lid can further be defined as a body area and assessed independent of the under eye and outer eye corner areas.

The assessment of each body area is based on observable characteristics of the body area. One or more characteristics may be associated with each body area. This assessment can be performed based on a straight observation of the area by the subject or by a third party such as a cosmetic surgeon, beautician, or therapist. For example, assessment data may be collected using a survey either completed as a self assessment by the subject or by a consultant such as a therapist or cosmetic surgeon based on observation of the subject. The assessment may also be performed using an automated video assessment technique. The assessment of each area is based on apparent signs of aging specific to the area. For example a rating system as illustrated in table 1 may be used:

TABLE 1

| Rating | Aging scale |
|---|---|
| A | Youthful: no discernable signs of aging |
| B | Mild: barely perceptible signs of aging |
| C | Moderate: perceptible signs of aging |
| D | Severe: distinct signs of aging |
| E | Extreme: extreme signs of aging |

Distinguishing between ratings for each area is based on the severity of aging signs such as the permanence and dept of wrinkles or discoloration. A guide for each area outlining the signs of aging and/or guidelines for distinguishing may be used to distinguish between ratings. For example, the difference between youthful and mild aging in relation to crows feet can be determined based on whether lines appear on movement, such as smiling, or not. Whereas the difference between severe aging and extreme aging can be based on the depth and number of permanent crows feet wrinkles.

Figure 4:
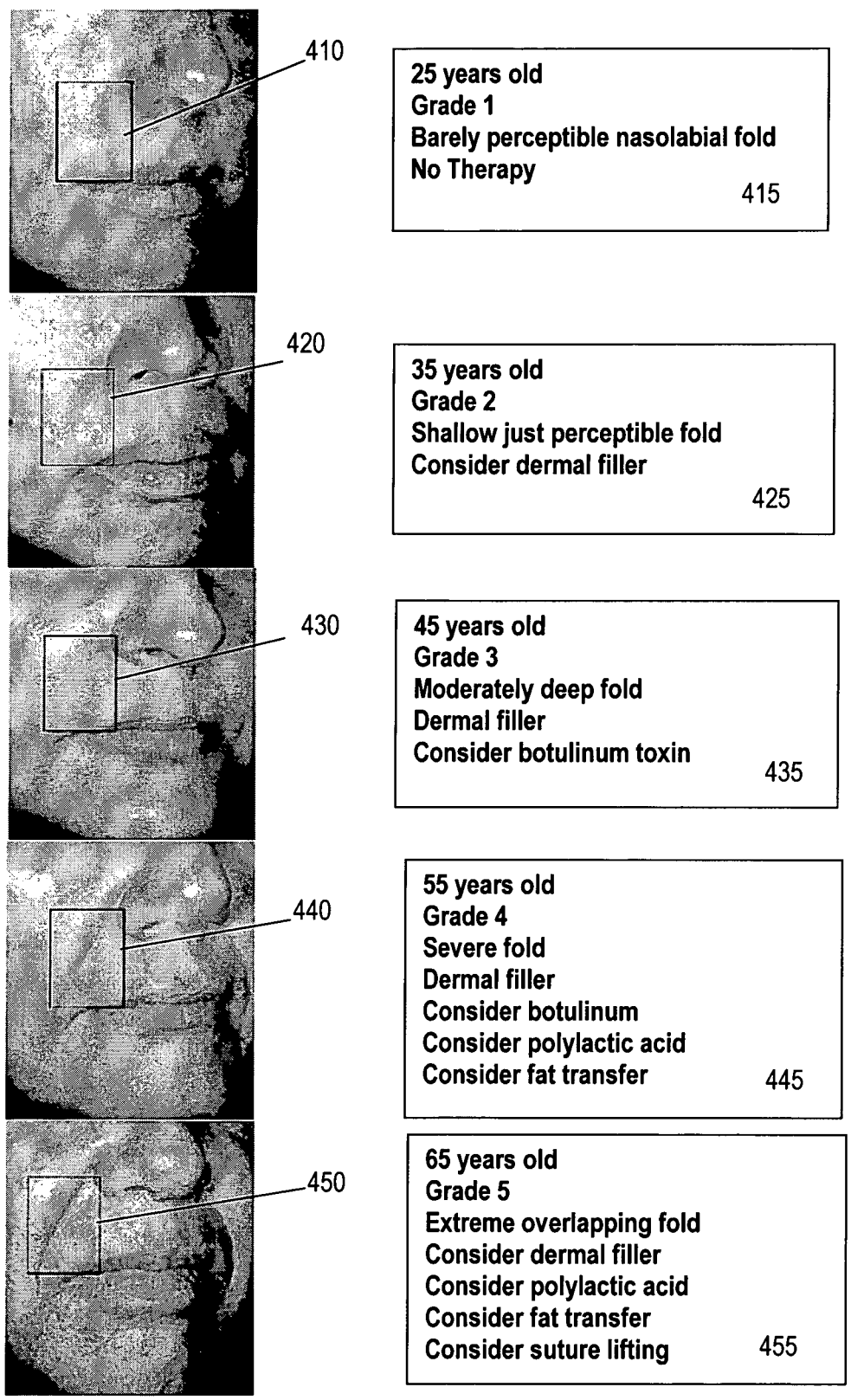
FIG. 4 An example of images used for guiding assessment of body area characteristics.

In an alternative embodiment images of examples of the appearance of each body area at different rankings may be provided. For example, for each body area a sequence of images showing different levels of aging may be provided and the user select the image which corresponds most closely with the observable characteristics of the body area of the subject. Such images may be provided in an electronic form, such as digital image files published on an Internet web site or computer readable media such as a CD or in a hardcopy form, say printed in a book or poster. FIG. 4 illustrates a sequence of such images focusing on the nasolabial fold area. The sequence of images show an example of the nasolabial fold area of a 25 year old 410, a 35 year old 420, a 45 year old 430, a 55 year old 440 and a 65 year old 450 a description 415, 425, 435, 445 and 455 may also be provided for each image, the description may also include treatment suggestions.

The images may be photographs of body areas of exemplary subjects, computer generated images, illustrations or caricatures of the observable characteristics of each body area. Images may be supplemented with a description of the characteristic and of aging indicators for the characteristic to assist making an assessment. Alternatively assessment of each area may be based on an collation of assessment values for individual characteristics of an area, so a subject can answer a series of questions like "Do your crows feet only appear when smiling?" with YES/NO or multiple choice answers, rather than a subject having to decide on a ranking for an area. Alternatively assessment may be performed for an area of the body based on a comparison of a stored image and a newly captured image of the body area of the subject being assessed. For example, an image of the back of a person's hand may be captured by a digital video or still camera and displayed along side an image selected from a set of stored images for the area. The assessor can then input an assessment based on a comparison of the two images, for example in response to the question "Which image appears older?" or "In which image do the veins appear more prominent?" The input response can then be used as assessment data. Alternatively, the assessor's response can be used to select a further image to display and/or question to ask to invoke a further response until given criteria are satisfied for the assessment data. For example, criteria for assessment data for a hand may require an assessor to have viewed 3 images and selected the one closest in apparent age to the captured image and given responses in respect of vein appearance, wrinkles, skin tone, calluses and finger nail appearance.

Assessing each body area individually in this manner, isolated from other body areas, targets the assessment to the particular characteristic of interest and the assessment can be performed more objectively than an assessment where an overall impression of a subject's appearance is used. Assessing each body area in isolation also means an impartial assessment of each body area can be performed which, in turn, avoids the impression of subjective "before" and "after" style assessments.

Figure 2:
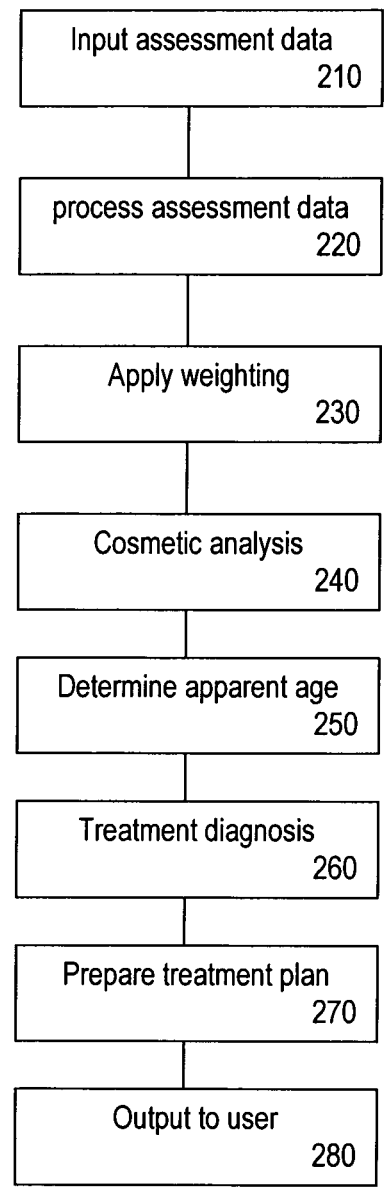
FIG. 2 A flowchart illustrating an embodiment of a cosmetic analysis method.

The assessment data for each body area is input 210 to the system 100 for cosmetic analysis as illustrated in FIG. 2. The assessment data is processed 220 and a weighting applied 230 for each body area. For example processing the assessment data may comprise interpreting answers to survey questions and selecting a defined numerical value associated with the answer or translation of an A-E ranking into a numerical value. This value may then have a weighting function applied to convert the assessment data into weighted data. For example, the value may be multiplied by a weighting value for the area of the body to provide a weighted value for the body area. Alternatively processing the assessment data and applying a weighting may comprise interpreting an A-E ranking for a body area by using the ranking to look up a defined weighted value for the body area.

In an embodiment the weighting applied for each area of the body is based on the relationship between an aging rating of the area of the body and overall subject age. An apparent age for the body area can be associated with each ranking, for example A 25 years, B 35 Years, C 45 years, D 55 years and E 65+ years. For each area of the body a numerical weighting can be specified for each ranking which relates the apparent age of the area to the contribution to overall subject age. The cosmetic analysis module applies the weighting for each area in accordance with the assessed ranking. It should be appreciated that as each area is assessed independently not all body areas of the subject may exhibit the same apparent age. Some areas may appear more or less youth-full than others. The weighting applied for each area of the body may also take into consideration the influence of a particular body area on the overall apparent age of the subject. For example, neck wrinkles may have more influence on the apparent age of a person than facial wrinkles.

Figure 3:
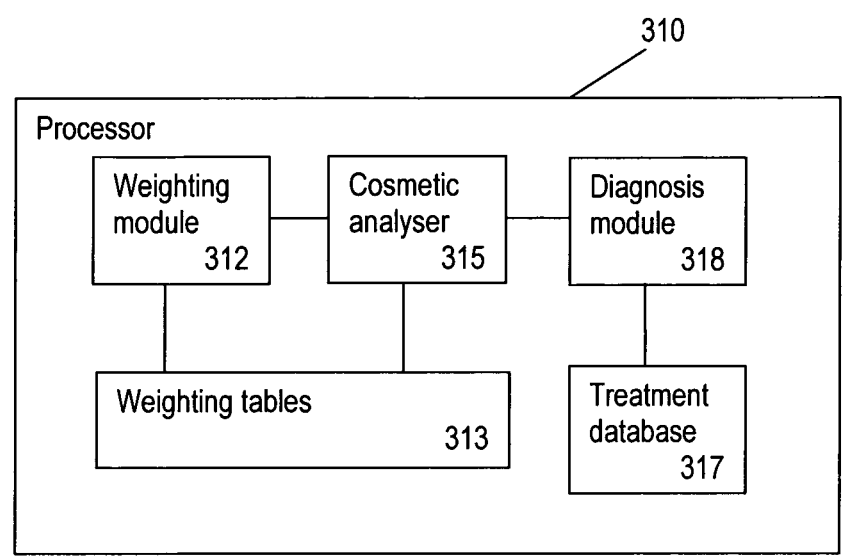
FIG. 3 A functional block diagram of an embodiment of the invention.

An embodiment of a cosmetic analysis module implemented in a processor is illustrated in FIG. 3, in this embodiment the functions of the cosmetic analysis module are implemented as software executable by the processor 310. In an embodiment, as illustrated in FIG. 3, a weighting module 312 is provided to apply the weighting to the assessment data in accordance with weighted values provided in a look-up table 313 or database accessible by the processor. In this embodiment the weighting module 312 looks up the appropriate weighted value in the table based on the input rank and body area, each looked up weighted value becomes an item in a set of weighted data which can then be analysed, by an cosmetic analyser 315, to generate cosmetic analysis data. The weighting tables 313 or database may be accessed over a network, such as the Internet. In this embodiment the weighting value for each ranking for each body area is predefined. Different weighting tables may be provided for each gender and optionally weighting tables based on race or ethnicity may also be provided. In an alternative embodiment a plurality of mathematical weighting functions may be defined based on one or more of the body area, gender and race or ethnicity, and the mathematical weighting functions applied to an aging value for each area determined from the assessment data.

Cosmetic analysis 240 is performed on the weighted data to determine the subject's apparent age 250. In an embodiment the subject's apparent age is determined by summing weighted values and comparing the sum total with benchmark or predetermined sum values for each age. The benchmark sum values can be based on analysed data of a model subject typical of the age or based on theoretical or statistical model characteristic data.

An advantage of the weighting system is that cosmetic analysis 240 can also determine the relative influence of areas of the body on the subject's apparent age. Where an area of the body is assessed at a relatively higher ranking than other most areas of the body, this area may have a greater influence on the apparent age than other areas based on the weighting applied to the area. For example, the relative influence of each area can be determined by analysing the weighted data. The analysis may be based on a comparison of the weighted values, the greatest having the most influence or a percentage analysis. The cosmetic analysis may also take into consideration related areas, for example areas related to a particular facial area or feature such as the eyes, neck, mouth or hands. A plurality of related areas each having relatively high weighted values may be determined to be more influential to the subject's apparent age than another isolated body area having a relatively high weighting value.

The weighting applied to the assessment data for each area of the body can also be based on subject gender. Different characteristics may also be defined for assessment for different genders. The advantage of applying different weighting values based on gender is that characteristics of areas of the body can have a different effect on the apparent age depending on the gender of the subject, further the amount of variation in some characteristics at different ages can vary between male and females. For example, hairlines and hair thickness are influential to apparent age for both men and women. However, for men, hairlines and hair thickness can vary significantly between different ages. Whereas hairlines and hair thickness does not vary as much over different ages in women as in men.

In the embodiment illustrated in FIG. 3, the cosmetic analyser 315 may optionally reference the weighting look up tables 313 during cosmetic analysis.

Determining the body areas influencing the apparent age of the subject can also be based on comparing the actual age and apparent age of the subject. For example the look up tables 313 may be referred by the cosmetic analyser 315 for assessing the relative influence of different body areas on the apparent age by looking up weighted values for a body area based on the subject's actual age and comparing this with the weighted data. Thus, where a subject's apparent age is older than their actual age, the body areas causing this older appearance can be identified. Where a subject's apparent age is the same or younger than their apparent age, the cosmetic analysis data can also be analysed to identify which areas of the body appear younger than their actual age and which appear older. This data can be useful to identify which body areas may benefit from remedial treatment compared to maintenance treatment.

Assessment of body areas for the influence on apparent aging can also be based on the assessment results for groups of characteristics, wherein the groups are defined by body area. For example, assessment results for characteristics of the forehead and hairline region may form one group and assessment results for the eye region may form another group. The weighted values for each group can be summed and a relative influence value for the group determined.

Embodiments can also include a treatment diagnosis module 318 adapted to determine one or more suggested treatments 260 for each of one or more body areas. The diagnosis module 318 may be implemented in the processor 310 or in a separate processor. For example, cosmetic analysis data may be sent via the internet to an independent diagnosis processor for treatment diagnosis. The treatment diagnosis module may have access to a treatment database 317 storing data relating to a plurality of available treatments. The treatment database 317 may be accessed via a network, such as the internet. In an alternative embodiment weighting values and treatment options are provided in a single look up table or database. Alternatively more than one treatment database maybe provided and the diagnosis module adapted to request treatment data from one or more of these databases, for example a database may be provided by each treatment supplier. The diagnosis module can be adapted to interpret treatment recommendations provided by each treatment supplier in the context of the subject's cosmetic analysis and select a subset of available treatments to suggest for the subject. The diagnosis module may return a plurality of treatment options for each body area.

The treatment module can diagnose appropriate treatment for every body area or selected body areas. The number of body areas and number of treatments proposed for each body area may be specified by a user. Treatments may be diagnosed and ranked based on the relative influence of the body area on the apparent age or other criteria. The criteria may be specified by a user, such as the subject, a cosmetic surgeon or therapist. For example, a user or skin therapist may specify only non-invasive or non-surgical treatments can be proscribed. Alternatively a cosmetic surgeon may specify that only specific surgical or invasive treatments may be suggested based on the wishes of the subject, the capabilities of the surgeon's practice, or regulatory restrictions. Other criteria may include allergies, surgical/non-surgical treatment preferences, cost constraints, time constraints, local treatment or product availability etc.

The treatment diagnosis module can be further adapted to develop a treatment plan 270 for the subject. The treatment plan may include a list of recommended treatments for each body area. The treatment plan may also include a treatment time schedule. For example the treatment time schedule may suggest timing and order for surgical procedures or suggested groupings for complementary treatments. The treatment diagnosis processor can also be adapted to identify any incompatible treatments. For example where two products which may be appropriate to treat two different characteristics have been identified as appropriate treatments individually but the two products may give rise to adverse side effects if used together, this can be identified and the appropriate warnings and scheduling recommendations included in the treatment plan. The treatment plan may also be developed based on user specified criteria, such as a time period available for treatment or treatment preferences.

The cosmetic analysis data, treatment diagnosis and treatment plan can be output 280 for use by the cosmetic surgeon, therapist or subject. The cosmetic analysis and treatment data may be presented in a report form for discussion between the subject and therapist. After a discussion information such as subject treatment preferences or limitation criteria can be entered in to the treatment diagnosis module and an updated or tailored treatment diagnosis report or treatment plan provided. Several iterations of discussion and reanalysis of the treatment plan may be performed before a final plan is decided.

Alternatively the cosmetic analysis and treatment data may be presented in an interactive form on a display, for example on a computer embodying the system and used to input the assessment ranking data. Interactive presentation of cosmetic analysis and treatment data can enable a subject and therapist or cosmetic surgeon to discuss treatment options and select treatments to be performed. These selections may be fed back into the treatment diagnosis module to provide an updated treatment plan.

Further the subject's cosmetic analysis data can be stored for comparison against a future assessment performed after one or more treatments have been performed. The comparison can provide feedback regarding body areas having changed ratings and hence feedback in relation to the effectiveness of the one or more treatments. For example, during the course of a treatment plan, effectiveness of completed treatments can be assessed by performing a new cosmetic analysis to compare with the original cosmetic analysis data.

Embodiments of the system can be provided as a stand alone apparatus or provided in the form of software modules and data which enable the system to be implemented on a generic processing device such as a computer or using a plurality of networked devices such as computers, servers and databases connected via a communication network such as the Internet. An embodiment of the system is envisaged comprising a computer readable media storing program instructions and data to implement an embodiment of the system on a stand alone computer. Alternatively, a system may be implemented utilising a network such as the Internet, enabling users to access the system via a secure Internet web page using a security key to input assessment data and receive cosmetic analysis and treatment data. Security keys may be issued via a user registration process or provided in conjunction with marketing or educational material for the system, such as a book or CD, in which assessment instructions, exemplary aging series of images and guidelines are published. For example, a user purchasing the book may be offered a key for free access to use the system, whereas a user not purchasing the book may be required to register and pay a fee to obtain a security key in order to use the system.

Alternatively, an interface to the system can be provided as a software application which can be downloaded to a mobile phone, PDA or other user device. A security key may be provided along with the download, created for the user device, or the user device identifier may be used for the security access code. For example, users of an i-phone or other mobile phone may be able to download an application which provides access to the secure web site. The user registers to download the application using their phone via an application server. During the course of this registration the application server acquires the phone identifier, for example an International Mobile Equipment Identifier (IMEI) or International Mobile Subscriber Identifier (IMSI), which is stored to use as the security access code. When the user opens the application the phone identifier is provide to the server for verification to enable access to the secure web site. The user can then enter assessment data using the mobile device for processing via the cosmetic analysis module resident on the server.

In an embodiment where an application is provided on a mobile phone, personal computer or other device which has an embedded or connected digital camera, the application may be adapted to use an image of the subject, captured using the camera, for acquiring assessment data. For example, an image of the subject's face can be captured using the digital camera. This captured image can be mapped by the application to identify areas of the face for assessment, for example nasolabial fold area, crow's feet, brow, areas of the hair line etc. The specific areas of the subject's face can then be displayed in isolation or beside a comparison image for assessment. The user may not realise which image is extracted from their face and which is the stored comparison image. This can further enhance the objectiveness of the assessment, as each area is viewed in isolation. Once the user has entered the assessment data for each area, the assessment data can be transmitted to the cosmetic analysis server for cosmetic analysis and treatment diagnosis. In some embodiments some of the cosmetic analysis may be implemented by the application running on the phone, for example converting the input assessment data to a ranking or weighting may be performed by the phone application, whereas the cosmetic analysis and treatment diagnosis is performed by the cosmetic analysis server. In an alternative embodiment, the downloadable application may also perform the cosmetic analysis and treatment diagnosis. This application may be a scaled down version of the cosmetic analysis system, adapted only to assess a few designated areas, for example, crows feet, brow wrinkles, lips and neck. Treatment plans for such an embodiment may be limited to only non-surgical, over the counter or lifestyle change, treatment actions. Over the counter treatments may include recommendations for skin care or cosmetic products and lifestyle change treatments may include actions such as increasing water or vitamin consumption, wear sunglasses, sleep advice, exercises, quit smoking etc.

Embodiments of the system may be implemented as a module in a medical practice system. For example a medical practice system may incorporate modules for cosmetic analysis, skin care and skin type analysis, treatment diagnosis, imaging, storage and management of electronic patient records, appointment scheduling, and accounting functions. Alternatively an embodiment of the cosmetic analysis system may be adapted to output data, such as cosmetic analysis data and treatment data in a format compatible with an electronic patient record system or other medical practice management system to enable recording of cosmetic analysis and treatment data directly into a patient's record.

In the claims which follow and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in any country.

EXAMPLE 1

The following example illustrates sections of weighting value look-up tables including suggested treatments for a plurality of treatment areas. Table A is a section of a look up table developed for Caucasian females and Table B is a look up table developed for Caucasian males.

TABLE A

| Rank | Weighting | Description | Treatment |
|---|---|---|---|
| | | Jaw line | |
| A | 1 | Tight, no redundancy | No therapy |
| B | 2 | Soft jaw line definition | RF tightening (eg. Thermacool), botulinum toxin |
| C | 3 | Some blurring of jaw line and redundancy of tissues with mild jowl formation | RF tightening (eg. Thermacool), botulinum toxin |
| D | 5 | Indistinct jaw line with quite obvious jowls | RF tightening (eg. Thermacool), dermal fillers, suture or surgical lifting |
| E | 8 | Significant sagging obliterating jaw definition, severe jowls | Suture lifts or surgical face lifting |
| | | Neck bands | |
| A | 1 | None | No therapy |
| B | 2 | Mild vertical banding on certain facial movements, little or no horizontal bands | Botulinum toxin |
| C | 4 | Moderate vertical banding on facial movement and mild to moderate at rest, beginnings of horizontal bands | Botulinum toxin, dermal fillers |

TABLE A-continued

| Rank | Weighting | Description | Treatment |
|---|---|---|---|
| D | 7 | Moderate to severe vertical banding on movement and moderate severe at rest with moderate redundancy, moderate to severe horizontal banding | Botulinum toxin, suture or surgical neck lifting |
| E | 10 | Severe vertical banding on movement and severe at rest with severe redundancy, moderate to severe horizontal banding | Suture or surgical neck lifting |
| | | Crows Feet | |
| A | 1 | None | No therapy |
| B | 2 | Lines only on movement | Eye skin care, +/− Botulinum toxin |
| C | 3 | Moderate lines only on movement and mild at rest | Eye skin care, botulinum toxin, Consider fractional resurfacing lasers |
| D | 5 | Severe lines only on movement and moderate at rest | Eye skin care, botulinum toxin, fractional resurfacing laser, plasma resurfacing or erbium laser resurfacing |
| E | 7 | Severe lines only on movement and severe at res | Eye skin care, plasma resurfacing, erbium or CO2 laser resurfacing |

A subject, Jenny a 35 year old female, performs an assessment and inputs results: Jaw line=A, Neck bands=C, and Crows feet=C, along with other results for the rest of the table. The overall apparent age for Jenny determined by the cosmetic analysis is 40 years old.

In Table A and A rating indicates characteristics of a 25 year old female and a C rating indicate characteristics of a 45 year old female.

The cosmetic analysis data output can indicate that Jenny's neck bands and crows feet have a significant influence on her apparent age. The data can also include the suggested treatments. An example of the report is given below.

Cosmetic analysis for: Jenny
Actual age: 35
Apparent age: 40
Treatment target area 1: Crows Feet
Assessed feature age: 45
Suggested treatment:
   1. Eye skin care
   2. Botulinum toxin
   3. Consider fractional resurfacing lasers
Treatment target area 2: Neck bands
Assessed feature age: 45
Suggested treatment:
   1. Botulinum toxin
   2. Dermal fillers Jenny can use the report to discuss treatment and maintenance with her therapist or cosmetic surgeon. Once preferred treatments have been decided this can be input to the system to generate a treatment plan. An example is given below:

Cosmetic analysis for: Jenny
Actual age: 35
Apparent age: 40
Clinical treatment plan:
Treatment target area 1: Crows Feet Assessed feature age: 45
Planned treatment:
  Botulinum toxin
Treatment date scheduled: 29 Mar. 2009
Treatment target area 2: Neck bands
Assessed feature age: 45
Planned treatment:
  Dermal fillers
Treatment date scheduled: 29 Mar. 2009
Ongoing care treatment plan:
Treatment target area 1: Crows Feet
Assessed feature age: 45
Prescribed treatment:
  Eye skin care:
Daily: Moisturise area morning & night (recommended products)
  Wear sunglasses in bright or sunny environments.
  5 minute eye relaxation exercises twice daily
Weekly: 20 minute cold compress.
Treatment target area 2: Neck bands
Assessed feature age: 45
Prescribed treatment:
  Skin care:
Daily: Moisturise area morning & night (recommended products).
  Wear sunscreen (recommended products)
Monthly: Firming mask (recommended products)

Table B, below, is a section of a table for Caucasian males. It can be observed from comparing Table A and Table B that although the descriptions and weighting values for some body areas may be the same for both males and females, the recommended treatments may vary between males and females, for example based on the different skin characteristics of males and females.

TABLE B

| Rank | Weighting | Description | Treatment |
|---|---|---|---|
| Jaw line | | | |
| A | 1 | Tight, no redundancy | No therapy |
| B | 2 | Soft jaw line definition | Thermage, botulinum toxin |
| C | 3 | Some blurring of jaw line and redundancy of tissues with mild jowl formation | Thermage, dermal fillers, botulinum toxin |
| D | 5 | Indistinct jaw line with quite obvious jowls | Thermage, dermal fillers, suture lifting |
| E | 8 | Significant sagging obliterating jaw definition, severe jowls | Suture lifting |
| Neck bands | | | |
| A | 1 | None | No therapy |
| B | 2 | Mild vertical banding on certain facial movements, little or no horizontal bands | Botulinum toxin |
| C | 4 | Moderate vertical banding on facial movement and mild to moderate at rest, beginnings of horizontal bands | Botulinum toxin |
| D | 7 | Moderate to severe vertical banding on movement and moderate severe at rest with moderate redundancy, moderate to severe horizontal banding | Suture lifting |
| E | 10 | Severe vertical banding on movement and severe at rest with severe redundancy, moderate to severe horizontal banding | Suture or surgical neck lifting |

TABLE B-continued

| Rank | Weighting | Description | Treatment |
|---|---|---|---|
| Crows Feet | | | |
| A | 1 | None | No therapy |
| B | 2 | Lines only on movement | Eye skin care, +/− Botulinum toxin |
| C | 3 | Moderate lines only on movement and mild at rest | Eye skin care, botulinum, Fraxel laser |
| D | 5 | Severe lines only on movement and moderate at rest | Eye skin care, botulinum toxin, Fraxel laser, Portrait plasma resurfacing or erbium laser resurfacing |
| E | 7 | Severe lines only on movement and severe at res | Eye skin care, Portrait plasma resurfacing or erbium laser resurfacing |

The invention claimed is:

1. A computer implemented cosmetic analysis method comprising the steps of:
   a) receiving assessment data of observable characteristics of each of a plurality of defined body areas of a subject via at least one input interface connected to a processor, wherein said observable characteristics are characteristic types for said observable characteristics for each said defined body area are indicative of aging for said body area, and each said defined body area is assessed based on a combination of said observable characteristics for said defined body area;
   b) converting said assessment data for each of said plurality of defined body areas to weighted data associated with each body area by determining from said assessment data for each said characteristic of said body area in combination with an aging rating value for each said body area, and applying to each said aging rating value a weighting for said body area relating a contribution of said aging rating of said body area to an overall subject apparent age to provide said weighted data, said step of converting said assessment data to said weighted data is performed by at least one cosmetic analysis module;
   c) generating cosmetic analysis data from said weighted data, said cosmetic analysis data providing a set of a plurality of apparent aging values, each said apparent aging value of said set being associated with a region of a body comprising two or more defined body areas related to a particular feature, wherein said apparent aging value for said region is based on said weighted data for said two or more defined body areas of said region;
   d) outputting said cosmetic analysis data via at least one output interface connected to said processor; and
   e) diagnosing and suggesting one or more treatments for each of said body areas via said at least one output interface, said step of diagnosing and suggesting one or more treatments for each of said body areas is performed by at least one treatment diagnosis module.

2. The method as claimed in claim 1, wherein said cosmetic analysis data includes a subject specific skin type value.

3. The method as claimed in claim 2 further comprising the step of determining body areas providing greatest influence on said overall subject apparent age value.

4. The method as claimed in claim 2 further comprising the step of ranking body areas based on relative contribution to said overall subject apparent age value.

5. The method as claimed in claim 1, wherein said applied weighting for each area of said body is based on subject gender.

6. The method as claimed in claim 1, wherein said applied weighting for each area of said body is based on subject ethnicity.

7. The method as claimed in claim 1 further comprising the step of ranking suggested treatments based on given criteria.

8. The method as claimed in claim 7, wherein said given criteria is specified by a user.

9. The method as claimed in claim 1 further comprising the step of ranking suggested treatments based on influence of said body area for which said treatment is suggested on said subject apparent age.

10. The method as claimed in claim 1 further comprising the step of developing a treatment plan for said subject.

11. The method as claimed in claim 1, wherein said treatment plan is based on specified criteria.

12. The method as claimed in claim 11, wherein said criteria including one or more of subject permitted surgical and non surgical criteria, complementary treatment grouping, body area treatment grouping, and specified treatment or recovery times.

13. The method as claimed in claim 1, wherein said assessment data is the result of a survey.

14. The method as claimed in claim 13 further comprising the step of a subject performing a self assessment survey.

15. The method as claimed in claim 1 further comprising before said step of receiving assessment data of observable characteristics the steps of:
   presenting a sequence of images to a user via at least one output interface;
   presenting to said user via said output interface one of a description of at least one observable characteristic of at least one body area of a subject and of at least one indicator for said observable characteristic which supplements said sequence of images respectively, and a captured image of said body area of said subject allowing a comparison of said captured image and said sequence of images for selection based on said observable characteristic; and
   selecting by said user at least a first image from said sequence of images which corresponds most closely with said observable characteristic.

16. The method as claimed in claim 1 further comprising the step of determining said subject apparent age by summing said weighting to provide a sum total weighting and comparing said sum total weighting with a predetermined sum value for each age of said set of apparent aging values, said predetermined sum value is based on a model selected from the group consisting of analyzed data of a model subject typical of each of said age, a theoretical model characteristic data, and a statistical model characteristic data.

17. A non-transitory computer readable storage medium, wherein a computer program product is stored thereon comprising a plurality of instructions for execution by a processor, which when executed, causes the processor to perform the steps of:
   receiving assessment data of observable characteristics of each of a plurality of defined body areas of a subject via at least one input interface connected to a processor, wherein said observable characteristics are characteristic types for said observable characteristics for each said defined body area are indicative of aging for said body area, and each said defined body area is assessed based on a combination of said observable characteristics for said defined body area;
   converting said assessment data for each of said plurality of defined body areas to weighted data associated with each body area by at least one cosmetic analysis module by determining from said assessment data for each said characteristic of said body area in combination with an aging rating value for each said body area, and applying to each said aging rating value a weighting for said body area relating a contribution of said aging rating of said body area to an overall subject apparent age to provide said weighted data;
   generating cosmetic analysis data from said weighted data, said cosmetic analysis data providing a set of a plurality of apparent aging values, each said apparent aging value of said set being associated with a region of a body comprising two or more defined body areas related to a particular feature, wherein said apparent aging value for said region is based on said weighted data for said two or more defined body areas of said region;
   outputting said cosmetic analysis data via at least one output interface connected to said processor; and
   diagnosing and suggesting one or more treatments for each of said body areas via said at least one output interface, said step of diagnosing and suggesting one or more treatments for each of said body areas is performed by at least one treatment diagnosis module;
   wherein said suggesting one or more treatments is based on output generated skin type and skin concerns and subject specific demographics.

18. The non-transitory computer readable storage medium as claimed in claim 17, wherein said applied weighting for each area of said body is based from the group consisting of subject gender, and subject ethnicity.

19. The non-transitory computer readable storage medium as claimed in claim 17 further comprising the steps of:
   determining body areas providing greatest influence on said overall subject apparent age value; and
   ranking body areas based on relative contribution to said overall subject apparent age value.

20. A cosmetic analysis system comprising:
   at least one processor;
   at least one input interface connected to said processor for receiving assessment data of one or more observable characteristics of each of each of a plurality of defined body areas of a subject, wherein said observable characteristics are characteristic types for said observable characteristics for each said defined body area are indicative of aging for said body area, and each said defined body area is assessed based on a combination of said observable characteristics for said defined body area;
   at least one non-transitory computer readable storage medium having a cosmetic analysis module is stored thereon comprising a plurality of instructions for execution by said processor, said instructions being configured for each said defined body area to:
      convert said assessment data for each of said plurality of defined body areas to weighted data associated with said defined body area by:
         determining from said assessment data for each said characteristic of said body area in combination with an aging rating value for each said body area; and
         applying to each said aging rating value a weighting for said body area relating a contribution of said aging rating of said body area to an overall subject apparent age to provide said weighted data;

generate cosmetic analysis data from said weighted data, said cosmetic analysis data providing a set of a plurality of apparent aging values, each said apparent aging value of said set being associated with a region of a body comprising two or more defined body areas related to a particular feature, wherein said apparent aging value for said region is based on said weighted data for said two or more defined body areas of said region; and an output interface connected to said processor for outputting said cosmetic analysis data.

* * * * *